(12) United States Patent
Hohlweg

(10) Patent No.: US 7,294,626 B2
(45) Date of Patent: *Nov. 13, 2007

(54) PIPERAZINES

(75) Inventor: Rolf Hohlweg, Humlebaek (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/334,207

(22) Filed: Jan. 18, 2006

(65) Prior Publication Data

US 2006/0173012 A1    Aug. 3, 2006

Related U.S. Application Data

(63) Continuation of application No. PCT/DK2004/000483, filed on Jul. 6, 2004.

(60) Provisional application No. 60/492,693, filed on Aug. 5, 2003.

(30) Foreign Application Priority Data

Jul. 29, 2003    (DK) .................. PA 2003 01107

(51) Int. Cl.
*C07D 403/04* (2006.01)
*C07D 403/14* (2006.01)
*A61K 31/496* (2006.01)

(52) U.S. Cl. .................. 514/252.02; 544/238
(58) Field of Classification Search ......... 544/238; 514/252.02

See application file for complete search history.

(56) References Cited

U.S. PATENT DOCUMENTS

| 4,673,675 A | 6/1987 | Robba et al. |
| 6,316,475 B1 | 11/2001 | Bennani et al. |

FOREIGN PATENT DOCUMENTS

| DE | 2804096 | 1/1978 |
| WO | 99/21845 | 10/1998 |
| WO | 00/66578 | 3/2000 |
| WO | 01/66534 | 3/2001 |
| WO | 01/74810 | 3/2001 |
| WO | 03/066604 | 2/2003 |
| WO | WO 03066604 A2 * | 8/2003 |

OTHER PUBLICATIONS

A.A. Hancock, Biochemical Pharmacology 71 (2006) 1103-1113.*
Walxzynski. K et al-Arch. Pharm. Med. Chem-1999-vol. 332-Part 11-pp. 389-398.
Giannangeli. Marilena et al-J Med Chem-1999-vol. 42-pp. 336-345.
Mokrosz. Jersy L. et al-J Med Chem-1992-vol. 35-pp. 2369-2374.
Abdel-Magid. Ahmed F. et al-J Org Chem-1996-vol. 61-pp. 3849-3862.
Prasad. Rai Nandan et al-J Med Chem-1968-vol. 11-Part 6-pp. 1144-1150.
Linney. I.D. et al-J Med Chem-2000-vol. 43-pp. 2362-2370.

* cited by examiner

*Primary Examiner*—Kahsay Habte
(74) *Attorney, Agent, or Firm*—Rosemarie R. Wilk-Orescan

(57) ABSTRACT

The present invention relates, inter alia, to novel piperazines of the following formula:

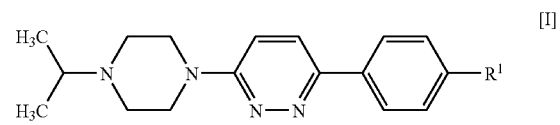

[I]

to the use of these compounds in the preparation of pharmaceutical compositions, to pharmaceutical compositions comprising the compounds, and to methods of treatment employing these compounds or compositions. The compounds show a high and selective binding affinity for the histamine H3 receptor, indicating histamine H3 receptor antagonistic, inverse agonistic or agonistic activity. As a result, the compounds are useful for the treatment of diseases or disorders related to the histamine H3 receptor.

12 Claims, No Drawings

PIPERAZINES

CROSS-REFERENCE TO RELATED APPLICATIONS

This application is a continuation of International Application Number PCT/DK2004/000483, filed Jul. 6, 2004, claiming priority of Danish Patent Application Number PA 2003 01107, filed Jul. 29, 2003, and U.S. Patent application No. 60/492,693, filed Aug. 5, 2003.

FIELD OF THE INVENTION

The present invention relates to novel piperazines, to the use of these compounds in pharmaceutical compositions, to pharmaceutical compositions comprising the compounds, and to methods of treatment employing these compounds or compositions. The present compounds show a high and selective binding affinity for the histamine H3 receptor, indicating histamine H3 receptor antagonistic, inverse agonistic or agonistic activity. As a result, the compounds are useful for the treatment of diseases or disorders related to the histamine H3 receptor.

BACKGROUND OF THE INVENTION

The existence of the histamine H3 receptor has been known for several years and the receptor is of current interest for the development of new medicaments. Recently, the human histamine H3 receptor has been cloned. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (ie it is active in the absence of an agonist). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Compounds similar to the compounds of the present invention have previously been disclosed, cf. *J. Med. Chem.* 1999, 42, 336, *J. Med. Chem.* 1992, 35, 2369, DE 2804096, *J. Org. Chem.* 1996, 61, 3849, *Bull. Soc. Chim. Fr.* 1969, 319, WO 00/66578, WO 99/21845, and *J. Med. Chem.* 1968, 11(6), 1144-1150. However, these references neither disclose nor suggest that these compounds may have a histamine H3 receptor antagonistic or agonistic activity.

Several publications disclose the preparation and use of histamine H3 agonists and antagonists. Most of these are imidazole derivatives. However, recently some imidazole-free ligands of the histamine H3 receptor have been described (see e.g. Linney et al., *J. Med. Chem.* 2000, 43, 2362-2370; U.S. Pat. No. 6,316,475, WO 01/66534 and WO 01/74810). However, these compounds differ structurally from the present compounds.

In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of piperazines has a high and specific affinity to the histamine H3 receptor.

Due to their interaction with the histamine H3 receptor, the present compounds are useful in the treatment of a wide range of conditions and disorders in which an interaction with the histamine H3 receptor is beneficial. Thus, the compounds may find use, e.g., in the treatment of diseases of the central nervous system, the peripheral nervous system, the cardiovascular system, the pulmonary system, the gastrointestinal system and the endocrinological system.

SUMMARY OF THE INVENTION

The invention relates to compounds according to formula I

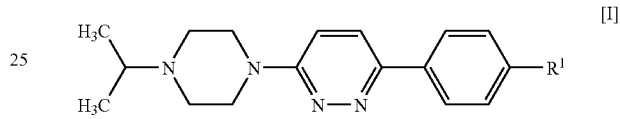

[I]

wherein $R^1$ is selected from fluoro, bromo, iodo, hydroxy, trifluoromethoxy, $C_{2-6}$-alkoxy, $C_{1-6}$-alkyl, amino, $C_{2-6}$-alkylsulfanyl (—SH—$C_{2-6}$-alkyl), $C_{2-6}$-alkylsulfinyl (—SO—$C_{2-6}$-alkyl), $C_{2-6}$-alkylsulfonyl (—S(=O)$_2$—$C_{2-6}$-alkyl), $C_{1-6}$-alkylamino, di-$C_{1-6}$-alkylamino, cyano, nitro, aryl, heteroaryl and $C_{3-8}$-cycloalkyl;

and pharmaceutically acceptable salts, solvates and prodrugs thereof.

The invention also relates to the use of said compounds in therapy, and in particular to pharmaceutical compositions comprising said compounds.

In another embodiment, the invention relates to methods of treatment, the method comprising administering to a subject in need thereof an effective amount of one or more compounds according to formula I.

In a still further embodiment, the invention relates to the use of compounds according to formula I in the manufacture of medicaments.

Definitions

In the structural formulae given herein and throughout the present specification, the following terms have the indicated meaning: The term "alkyl" as used herein represents a saturated, branched or straight hydrocarbon group having the indicated number of carbon atoms. Thus, the terms "$C_{1-3}$-alkyl", "$C_{1-6}$-alkyl" and "$C_{2-6}$-alkyl" as used herein represent saturated, branched or straight hydrocarbon groups having from 1 to 3 carbon atoms, 1 to 8 carbon atoms and 2 to 6 carbon atoms, respectively. Typical alkyl groups include, but are not limited to, methyl, ethyl, n-propyl, isopropyl, butyl, isobutyl, sec-butyl, tert-butyl, pentyl, hexyl and the like.

The term "$C_{2-6}$-alkoxy" as used herein refers to the radical —O—$C_{2-6}$alkyl, wherein $C_{2-6}$-alkyl is as defined above. Representative examples are ethoxy, n-propoxy, isopropoxy, butoxy, secbutoxy, tert-butoxy, pentoxy, isopentoxy, hexoxy, isohexoxy and the like.

The term "$C_{1-6}$-alkylamino" as used herein refers to the radical —NH—$C_{1-6}$-alkyl, wherein $C_{1-6}$-alkyl is as defined above. Representative examples are methylamino, ethylamino, isopropylamino, n-propylamino, butylamino, pentylamino, hexylamino and the like.

The term "di-$C_{1-6}$-alkylamino" as used herein refers to the radical —N($C_{1-6}$-alkyl)$_2$, wherein $C_{1-6}$-alkyl is as defined above. It should be understood that the $C_{1-6}$-alkyl groups may be the same or different. Representative examples are dimethylamino, methylethylamino, diethylamino, diisopropylamino, di-n-propylamino, dibutylamino, dipentylamino, dihexylamino and the like.

The term "$C_{3-8}$-cycloalkyl" as used herein represents a monocyclic, carbocyclic group having from from 3 to 8 carbon atoms. Representative examples are cyclopropyl, cyclobutyl, cyclopentyl and the like.

The term "$C_{2-6}$-alkylsulfonyl" as used herein refers to the radical —S(=O)$_2$-$C_{2-6}$-alkyl, wherein $C_{2-6}$-alkyl is as defined above. Representative examples are ethylsulfonyl, isopropylsulfonyl, n-propylsulfonyl, butylsulfonyl, pentylsulfonyl and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indanyl, indolinyl, oxazolidinyl, oxazolinyl, oxazepinyl and the like.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The term "effective amount" as used herein is intended to indicate an amount of a compound (in casu a compound according to formula I) which when administered a patient gives rise to a therapeutically relevant response. Said amount may vary depending on e.g. the sex, age, in the weight and condition of the patient. It lies within the skills of an ordinary trained physician to determine what an effective amount in any particular treatment is.

DETAILED DESCRIPTION OF THE INVENTION

In one embodiment, $R^1$ represents bromo or cyano.

The compounds of the present invention interact with the histamine H3 receptor and are accordingly believed to be particularly useful in the treatment of a variety of diseases or conditions in which histamine H3 interactions are beneficial.

In one aspect, the invention provides the use of a compound according to formula (I) in a pharmaceutical composition. The pharmaceutical composition may in another aspect of the invention comprise, as an active ingredient, at least one compound according to formula (I) together with one or more pharmaceutically acceptable carriers or excipients. In another aspect, the invention provides such a pharmaceutical composition in unit dosage form, comprising from about 0.05 mg to about 1000 mg, e.g. from about 0.1 mg to about 500 mg, such as from about 0.5 mg to about 200 mg of the compound according to formula (I).

In another aspect, the invention provides the use of a compound of formula (I) as defined above for the preparation of a pharmaceutical composition for the treatment of diseases and disorders in which an inhibition of the H3 histamine receptor has a beneficial effect.

In another aspect, the invention provides the use of a compound of formula (I) for the preparation of a pharmaceutical composition having histamine H3 antagonistic activity or histamine H3 inverse agonistic activity.

In another aspect the invention provides the use of a compound of formula (I) for the preparation of a pharmaceutical composition for the reduction of weight.

In another aspect, the invention provides the use of a compound of formula (I) for the preparation of a pharmaceutical composition for the treatment of overweight or obesity.

In another aspect, the invention provides the use of a compound of formula (I) for the preparation of a pharmaceutical composition for the suppression of appetite or for satiety induction.

In another aspect, the invention provides the use of a compound of formula (I) for the preparation of a pharmaceutical composition for the prevention and/or treatment of disorders and diseases related to overweight or obesity, such as dyslipidaemia, coronary heart disease, gallbladder disease, osteoarthritis and various types of cancer such as endometrial, breast, prostate and colon cancers.

In another aspect, the invention provides the use of a compound of formula (I) for the preparation of a pharmaceutical composition for the prevention and/or treatment of eating disorders, such as bulimia or binge eating.

In another aspect, the invention provides the use of a compound of formula (I) for the preparation of a pharmaceutical composition for the treatment of IGT (Impaired glucose tolerance).

In another aspect, the invention provides the use of a compound of formula (I) for the preparation of a pharmaceutical composition for the treatment of type 2 diabetes.

In another aspect, the invention provides the use of a compound of formula (I) for the preparation of a pharmaceutical composition for the delaying or prevention of the progression from IGT to type 2 diabetes.

In another aspect, the invention provides the use of a compound of formula (I) for the preparation of a pharmaceutical composition for the delaying or prevention of the progression from non-insulin requiring type 2 diabetes to insulin requiring type 2 diabetes.

In another aspect, the invention provides the use of a compound of formula (I) for the preparation of a pharmaceutical composition for the treatment of diseases and disorders in which a stimulation of the H3 histamine receptor has a beneficial effect.

In another aspect, the invention provides the use of a compound of formula (I) for the preparation of a pharmaceutical composition having histamine H3 agonistic activity.

In another aspect, the invention provides the use of a compound of formula (I) for the preparation of a pharmaceutical composition for the treatment of allergic rhinitis, ulcer or anorexia.

In another aspect, the invention provides the use of a compound of formula (I) for the preparation of a pharmaceutical composition for the treatment of Alzheimer's disease, narcolepsy, attention deficit disorders or reduced wakefulness, or for the regulation of sleep.

In another aspect, the invention relates to the use of a compound of formula (I) for the preparation of a pharmaceutical preparation for the treatment of airway disorders, such as asthma, for regulation of gastric acid secretion, or for treatment of diarrhoea.

In another aspect, the invention provides a method for the treatment of disorders or diseases related to the H3 histamine receptor, the method comprising administering to a subject in need thereof an effective amount of a compound of the general formula (I) as defined above, or of a pharmaceutical composition comprising such a compound.

In another aspect, the invention provides a method as described above, wherein the effective amount of the compound of the general formula (I) as defined above is in the range of from about 0.05 mg to about 2000 mg, preferably from about 0.1 mg to about 1000 mg, and more preferably from about 0.5 mg to about 500 mg per day.

In one aspect, the invention relates to compounds which exhibit histamine H3 receptor antagonistic activity or inverse agonistic activity and which may accordingly be useful in the treatment of a wide range of conditions and disorders in which histamine H3 receptor blockade is beneficial.

In another aspect, the invention provides a method for reduction of weight, the method comprising administering to a subject in need thereof an effective amount of a compound of formula (I) as defined above.

In another aspect, the invention provides a method for treatment of overweight or obesity, the method comprising administering to a subject in need thereof an effective amount of a compound of formula (I).

In another aspect, the invention provides a method for suppression of appetite or for satiety induction, the method comprising administering to a subject in need thereof an effective amount of a compound of formula (I).

In another aspect, the invention provides a method for prevention and/or treatment of disorders or diseases related to overweight or obesity, such as dyslipidaemia, coronary heart disease, gallbladder disease, osteoarthritis and various types of cancer, e.g. endometrial, breast, prostate or colon cancer, the method comprising administering to a subject in need thereof an effective amount of a compound of formula (I).

In another aspect, the invention provides a method for prevention and/or treatment of eating disorders, such as bulimia and binge eating, the method comprising administering to a subject in need thereof an effective amount of a compound of formula (I).

In another aspect, the invention provides a method for treatment of IGT (Impaired glucose tolerance), the method comprising administering to a subject in need thereof an effective amount of a compound of formula (I).

In another aspect, the invention provides a method for the treatment of type 2 diabetes, the method comprising administering to a subject in need thereof an effective amount of a compound of formula (I).

In another aspect, the invention provides a method for the delaying or prevention of the progression from IGT to type 2 diabetes, the method comprising administering to a subject in need thereof an effective amount of a compound of formula (I).

In another aspect, the invention provides a method for the delaying or prevention of the progression from non-insulin requiring type 2 diabetes to insulin requiring type 2 diabetes, the method comprising administering to a subject in need thereof an effective amount of a compound of formula (I).

In another aspect, the invention relates to compounds which exhibit histamine H3 receptor agonistic activity and which may accordingly be useful in the treatment of a wide range of conditions and disorders in which histamine H3 receptor activation is beneficial.

Compounds of the present invention may also be used for the treatment of airway disorders (such as asthma), as anti-diarrhoeals, and for the modulation of gastric acid secretion. Furthermore, compounds of the present invention may be used for the treatment of diseases associated with the regulation of sleep and wakefulness, and for the treatment of narcolepsy and attention deficit disorders.

Moreover, compounds of the invention may be used as CNS stimulants or as sedatives.

The present compounds may also be used for the treatment of conditions associated with epilepsy. Additionally, compounds of the invention may be used for the treatment of motion sickness and vertigo. Furthermore, they may be useful as regulators of hypothalamohypophyseal secretion, as antidepressants, as modulators of cerebral circulation, and in the treatment of irritable bowel syndrome.

Further, compounds of the present invention may be used for the treatment of dementia and Alzheimer's disease.

Compounds of the present invention may also be useful for the treatment of allergic rhinitis, ulcer or anorexia.

Compounds of the present invention may furthermore be useful for the treatment of migraine [see, e.g., McLeod et al., *The Journal of Pharmacology and Experimental Therapeutics* 287 (1998), 43-50] and for the treatment of myocardial infarction [see Mackins et al., *Expert Opinion on Investigational Drugs* 9 (2000), 2537-2542].

In a further aspect of the invention, treatment of a patient with a compound of the present invention is combined with diet and/or exercise.

In a further aspect of the invention, one of more compounds of the present invention is/are administered in combination with one or more further active substances in any suitable ratio(s). Such further active agents may, for example, be selected from antiobesity agents, antidiabetics, antidyslipidemic agents, antihypertensive agents, agents for the treatment of complications resulting from or associated with diabetes, and agents for the treatment of complications and disorders resulting from or associated with obesity.

Thus, in a further aspect of the invention one or more compounds of the present invention may be administered in combination with one or more antiobesity agents or appetite regulating agents. Such agents may, for example, be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention, an antiobesity agent administered in combination with one or more compounds of the invention is leptin.

In another embodiment, such an antiobesity agent is dexamphetamine or amphetamine.

In another embodiment, such an antiobesity agent is fenfluramine or dexfenfluramine.

In still another embodiment, such an antiobesity agent is sibutramine.

In a further embodiment, such an antiobesity agent is orlistat.

In another embodiment, such an antiobesity agent is mazindol or phentermine.

In still another embodiment, such an antiobesity agent is phendimetrazine, diethylpropion, fluoxetine, bupropion, topiramate or ecopipam.

In yet a further aspect of the invention, one or more compounds of the present invention may be administered in combination with one or more antidiabetic agents. Relevant antidiabetic agents include insulin, insulin analogues and derivatives such as those disclosed in EP 0 792 290 (Novo Nordisk A/S), e.g. $N^{\epsilon B29}$-tetradecanoyl des (B30) human insulin, EP 0 214 826 and EP 0 705 275 (Novo Nordisk A/S), e.g. $Asp^{B28}$ human insulin, U.S. Pat. No. 5,504,188 (Eli Lilly), e.g. $Lys^{B28}$ $Pro^{B29}$ human insulin, EP 0 368 187 (Aventis), e.g. Lantus®, all of which are incorporated herein by reference, GLP-1 derivatives, such as those disclosed in WO 98/08871 (Novo Nordisk A/S), incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells, e.g. potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists, such as one of those disclosed in WO 99/01423 and WO 00/39088 (Novo Nordisk A/S and Agouron Pharmaceuticals, Inc.), both of which are incorporated herein by reference, GLP-1 agonists, such as those disclosed in WO 00/42026 (Novo Nordisk A/S and Agouron Pharmaceuticals, Inc.), incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention, one or more compounds of the present invention may be administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention, one or more compounds of the present invention may be administered in combination with a sulfonylurea, e.g. tolbutamide, chlorpropamide, tolazamide, glibenclamide, glipizide, glimepiride, glicazide or glyburide.

In another embodiment of the invention, one or more compounds of the present invention may be administered in combination with a biguanide, e.g. metformin.

In yet another embodiment of the invention, one or more compounds of the present invention may be administered in combination with a meglitinide, e.g. repaglinide or nateglinide.

In still another embodiment of the invention, one or more compounds of the present invention may be administered in combination with a thiazolidinedione insulin sensitizer, e.g. troglitazone, ciglitazone, pioglitazone, rosiglitazone, isaglitazone, darglitazone, englitazone, CS-011/CI-1037 or T 174, or a compound disclosed in WO 97/41097, WO 97/41119, WO 97/41120, WO 00/41121 and WO 98/45292 (Dr. Reddy's Research Foundation), all of which are incorporated herein by reference.

In still another embodiment of the invention, one or more compounds of the present invention may be administered in combination with an insulin sensitizer, e.g. such as GI 262570, YM-440, MCC-555, JTT-501, AR-H039242, KRP-297, GW-409544, CRE-16336, AR-H049020, LY510929, MBX-102, CLX-0940, GW-501516, or a compound disclosed in WO 99/19313, WO 00/50414, WO 00/63191, WO 00/63192 or WO 00/63193 (Dr. Reddy's Research Foundation) or in WO 00/23425, WO 00/23415, WO 00/23451, WO 00/23445, WO 00/23417, WO 00/23416, WO 00/63153, WO 00/63196, WO 00/63209, WO 00/63190 or WO 00/63189 (Novo Nordisk A/S), all of which are incorporated herein by reference.

In a further embodiment of the invention, one or more compounds of the present invention may be administered in combination with an α-glucosidase inhibitor, e.g. voglibose, emiglitate, miglitol or acarbose.

In another embodiment of the invention, one or more compounds of the present invention may be administered in combination with an agent acting on the ATP-dependent potassium channel of the β-cells, e.g. tolbutamide, glibenclamide, glipizide, glicazide, BTS-67582 or repaglinide.

In yet another embodiment of the invention, one or more compounds of the present invention may be administered in combination with nateglinide.

In still another embodiment, one or more compounds of the present invention may be administered in combination with an antihyperlipidemic agent or antilipidemic agent, e.g. cholestyramine, colestipol, clofibrate, gemfibrozil, lovastatin, pravastatin, simvastatin, probucol or dextrothyroxine.

In still another embodiment of the invention, one or more compounds of the present invention may be administered in combination with an antilipidemic agent, e.g.

cholestyramine, colestipol, clofibrate, gemfibrozil, lovastatin, pravastatin, simvastatin, probucol or dextrothyroxine. In another aspect of the invention, one or more compounds of the present invention may be administered in combination with more than one of the above-mentioned compounds, e.g. in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, one or more compounds of the present invention may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of compounds according to the invention with diet and/or exercise, one or more of the above-mentioned compounds and optionally one or more other active substances are considered to be within the scope of the present invention.

Furthermore, some compounds of the present invention may exist in different tautomeric forms, and it is intended that any tautomeric forms which the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. Alternatively, the free base may be dissolved in a suitable solvent containing the appropriate acid, and the salt isolated by evaporating the solvent or otherwise separating the salt and solvent. Compounds of the present invention may form solvates with standard low molecular weight solvents using methods well known to the person skilled in the art. Such solvates are also to be understood as being within the scope of the present invention.

The invention also encompasses prodrugs of the present compounds which following administration undergo chemical conversion by metabolic processes before becoming active pharmacological substances. In general, such prodrugs will be functional derivatives of the present compounds which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques, such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route, such as the oral, rectal, nasal, pulmonary, topical (including buccal and sublingual), transdermal, intracistemal, intraperitoneal, vaginal or parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings, such as enteric coatings, or they can be formulated so as to provide controlled release of the active ingredient, such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also to be understood as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferably from about 0.05 to about 10 mg/kg body weight per day, administered in one or more doses, such as from 1 to 3 doses. The exact dosage will depend upon the frequency and mode of administration, the sex, age, weight and general condition of the subject treated, the nature and severity of the condition treated and any concomitant diseases to be treated, and other factors evident to those skilled in the art.

The formulations may conveniently be presented in unit dosage form by methods known to those skilled in the art. A typical unit dosage form for oral administration one or more times per day, such as from 1 to 3 times per day, may contain from 0.05 to about 1000 mg, preferably from about 0.1 to about 500 mg, and more preferably from about 0.5 mg to about 200 mg of a compound (or a salt or other derivative thereof as set forth above), according to the invention.

For parenteral routes, such as intravenous, intrathecal, intramuscular and similar administration, typical doses are of the order of about half the dose employed for oral administration. The compounds of this invention are generally utilized as the free substance or as a pharmaceutically acceptable salt thereof. One example is an acid addition salt of a compound having a free base functionality. When a compound of the formula (I) contains a free base functionality, such salts are prepared in a conventional manner by treating a solution or suspension of the free base form of the compound of formula (I) with a chemical equivalent (acid-base equivalent) of a pharmaceutically acceptable acid. Representative examples of relevant inorganic and organic acids are mentioned above. Physiologically acceptable salts of a compound of the invention having an hydroxy group include the anion of said compound in combination with a suitable cation, such as sodium or ammonium ion.

For parenteral administration, solutions of the novel compounds of the formula (I) in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylenes or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier may vary widely, but will usually be from about 25 mg to about 1 g. If a liquid carrier is used, the preparation may be in the form of a syrup, emulsion, soft gelatine capsule or sterile injectable liquid, such as an aqueous or non-aqueous liquid suspension or solution.

A typical tablet, which may be prepared by conventional tabletting techniques, may contain:

| | | |
|---|---|---|
| Core: | | |
| Compound of the invention, e.g. compound of any of Examples 1-8 (as free compound or salt thereof) | | 5.0 mg |
| Lactosum Ph. Eur. | | 67.8 mg |
| Cellulose, microcryst. (Avicel) | | 31.4 mg |
| Amberlite ® IRP88* | | 1.0 mg |
| Magnesii stearas Ph. Eur. | | q.s. |
| Coating: | | |
| Hydroxypropyl methylcellulose | approx. | 9 mg |
| Mywacett 9-40 T** | approx. | 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with one or more further pharmacologically active substances, e.g. substances chosen among those described in the foregoing.

EXAMPLES

In the examples the following terms are intended to have the following, general meanings:

DIPEA: diisopropylethylamine

DMSO: dimethylsulphoxide

NMR

NMR spectra were recorded on Bruker 300 MHz and 400 MHz instruments.

LC-MS

HPLC-MS was performed on a Perkin Elmer instrument (API 100). The column used was X-Terra C18, 5 μm, 50×3 mm, and elution was done at 1.5 ml/min at room temperature with a gradient of 5-90% acetonitrile in water with 0.01% trifluoroacetic acid over a period of 7.5 min.

HPLC

The RP-analyses was performed using an Alliance Waters 2695 system fitted with a Waters 2487 dual-band detector. UV detections were collected using a Symmetry C18, 3.5 um, 3.0 mm×100 mm column. The elution is done with a linear gradient consisting of 5-90% acetonitrile, 90-0% water and 5% of 1% aqueous trifluoroacetic acid over a period of 8 minutes at a flow-rate of 1.0 min/min.

General Procedure (A)

Compounds of the general formula (I) may be prepared by the general procedure (A):

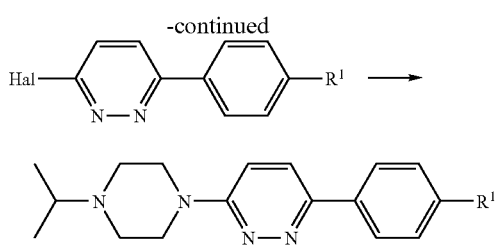

(Hal = halogen, notably Cl or Br)

A mixture of isopropylpiperazine (2.00 mmol), DMSO (1.0 ml), a suitable halopyridazine (2.00 mmol), and a base such as DIPEA (0.20 ml) is stirred for one hour at 100° C. and then for 18 hours at 120° C. Water and potassium carbonate are added and the mixture is extracted with a solvent such as ethyl acetate (3×20 ml). The combined extracts are washed with brine, dried over magnesium sulphate, and concentrated under reduced pressure. The residue may be converted into an appropriate salt, such as the hydrochloride salt, by co-evaporation with an acid, such as 1 molar aqueous hydrochloric acid, ethanol and toluene, and the residue is then purified by recrystallization General Procedure (B)

Compounds of the general formula (I) may be prepared by the general procedure (B):

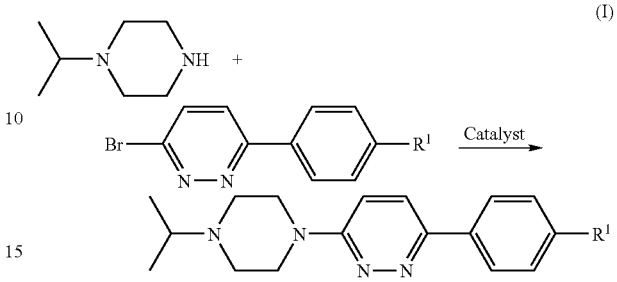

A compound of formula I may be prepared from a suitable monosubstituted piperazine and a suitable bromopyridazine in the presence of a suitable catalyst, such as, e.g., tris (dibenzylideneacetone)dipalladium, in a suitable solvent, such as toluene, at a suitable temperature between 0° C. and 150° C.

General Procedure (C)

Chloropyridazines of the general formula (IIa), (IIb) or (IIc) may be prepared by the general procedure (C):

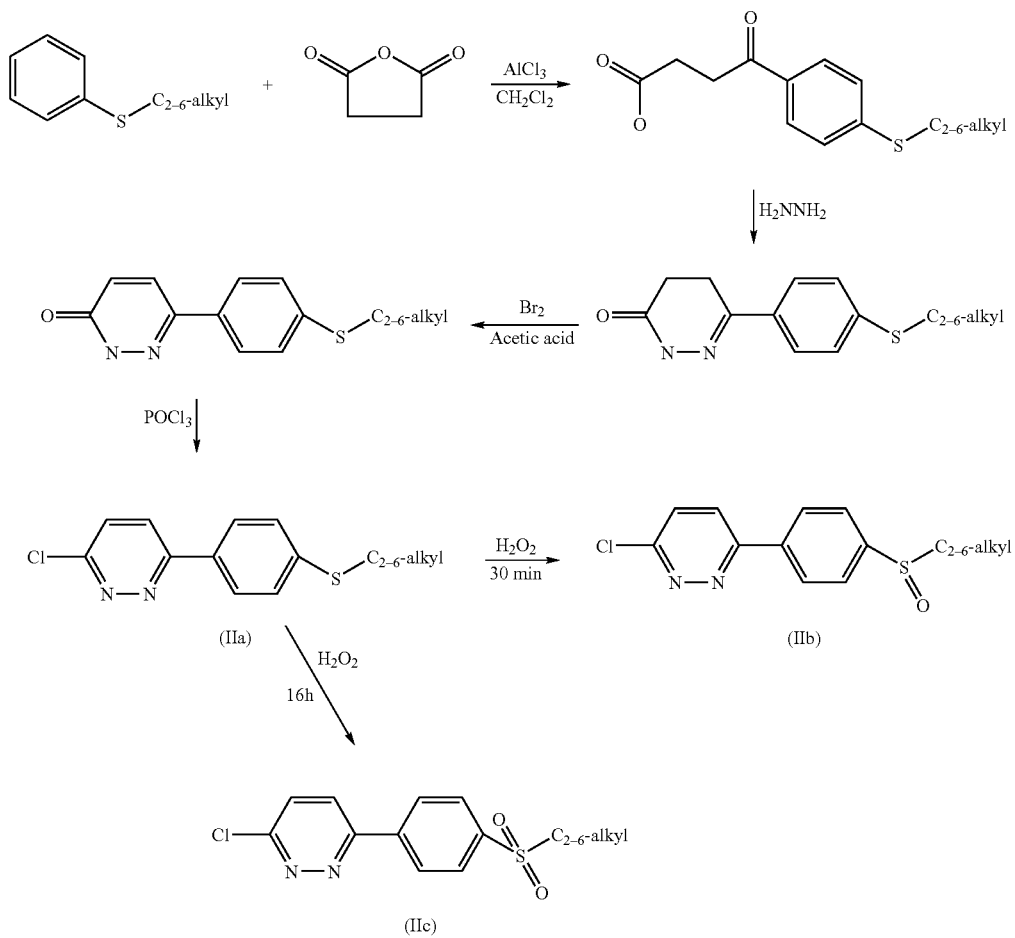

Example 1

4-[6-(4-Isopropylpiperazin-1-yl)-pyridazin-3-yl]benzonitrile

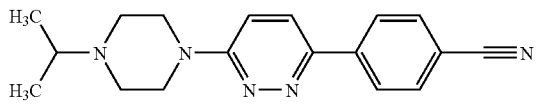

A suspension of 4-(6-chloro-pyridazin-3-yl)-benzonitrile (1 g, 4.64 mmol; prepared as described in U.S. Pat. No. 4,112,095), isopropylpiperazine (0.654 g, 5.1 mmol), DIPEA (1.199 g, 9.27 mmol) and 4-(dimethylamino)pyridine (0.057 g, 0.464 mmol) in DMSO (4 ml) was stirred and heated to 100° C. for 20 h. After cooling to room temperature, the mixture was diluted with dichloromethane (25 ml) and water (35 ml) and stirred for 5 min. The organic phase was separated, washed with water (50 ml) and brine (50 ml), and acidified to pH 2 by addition of 1 N hydrochloric acid. The mixture was extracted with water (30 ml), and the aqueous phase was washed with dichloromethane (10 ml) and concentrated in vacuo to give a solid, which was collected and stripped with ethanol to afford the title compound as a crystalline hydrochloride (1.33 g, 76%).

$^1$H NMR (D$_2$O) δ 1.30 (d, 6H), 3.26 (broad t, 2H), 3.45-3.68 (m, 5H), 4.52 (broad d, 2H), 7.75 (d, 1H), 7.77 (d, 2H), 7.87 (d, 2H), 8.12 (d, 1H); HPLC-MS: m/z 308.2 (MH$^+$); R$_t$: 1.76 min.

Example 2

3-(4-Bromophenyl)-6-(4-isopropylpiperazin-1-yl)pyridazine

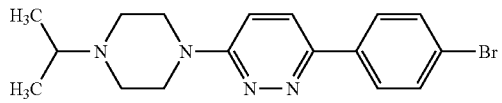

This compound was prepared according to General Procedure (A), starting from 1-isopropylpiperazine and 3-chloro-6-(4-bromophenyl)pyridazine, prepared as described in U.S. Pat. No. 4,112,095. The compound was isolated as its hydrochloride salt.

$^1$H NMR (D$_2$O): δ 1.30 (d, 6H), 3.23 (broad t, 2H), 3.47 (broad t, 2H), 3.52-3.67 (m, 3H, 4.52 (broad d, 2H), 7.64 (d, 2H), 7.67 (d, 2H), 7.82 (d, 1H), 8.15 (d, 1H); HPLC: R$_t$=3.49 min.

Example 3

3-(4-Ethanesulfonylphenyl)-6-(4-isopropylpiperazin-1-yl)pyridazine

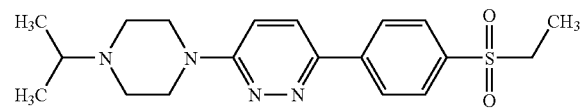

This compound was prepared according to General Procedure (A), starting from 1-isopropylpiperazine and 3-chloro-6-(4-ethanesulfonylphenyl)pyridazine, prepared according to General Procedure (C). The compound was isolated as its hydrochloride salt.

$^1$H NMR (d$_6$-DMSO): δ 1.15 (t, 3H), 1.33 (d, 6H), 3.17 (m, 2H), 3.36 (q, 2H), 3.45-3.60 (m, 3H), 3.67 (t, 2H), 4.66 (d, 2H), 7.71 (d, 1H), 8.00 (d, 2H), 8.29 (d, 1H), 8.33 (d, 2H); HPLC: R$_t$=4.73 min.

Example 4

3-(4-Ethanesulfinylphenyl)-6-(4-isopropylpiperazin-1-yl)pyridazine

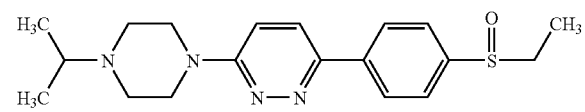

This compound was prepared according to General Procedure (A), starting from 1-isopropylpiperazine and 3-chloro-6-(4-ethanesulfinylphenyl)pyridazine, prepared according to General Procedure (C). The compound was isolated as its hydrochloride salt.

$^1$H NMR (d$_6$-DMSO): δ 1.06 (t, 3H), 1.32 (d, 6H), 2.83 (m, 1H), 3.05-3.24 (m, 3H), 3.46-3.59 (m, 3H), 3.68 (broad t, 2H), 4.64 (broad d, 2H), 7.75-7.83 (m, 3H), 8.26 (d, 2H), 8.32 (d, 1H), 11.47 (broad s, 1H); HPLC: R$_t$=4.10 min.

Example 5

3-[4-(Butane-1-sulfonyl)phenyl]-6-(4-isopropylpiperazin-1-yl)pyridazine

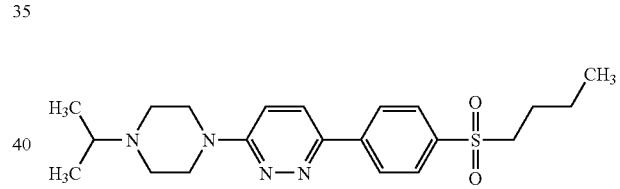

This compound was prepared according to General Procedure (A), starting from 1-isopropylpiperazine and 3-[4-(butane-1-sulfonyl)phenyl]-6-chloropyridazine, prepared according to General Procedure (C). The compound was isolated as its hydrochloride salt.

$^1$H NMR (d$_6$-DMSO): δ 0.84 (t, 3H), 1.33 (d, 6H), 1.3-1.4 (m, 2H), 1.54 (m, 2H), 3.17 (m, 2H), 3.37 (m, 2H), 3.45-3.60 (m, 3H), 3.67 (broad t, 2H), 4.66 (broad d, 2H), 7.73 (d, 1H), 8.03 (d, 2H), 8.30 (d, 1H), 8.34 (d, 2H), 11.41 (broad s, 1H); HPLC: R$_t$=6.46 min.

Example 6

3-[4-(Butane-1-sulfinyl)phenyl]-6-(4-isopropylpiperazin-1-yl)pyridazine

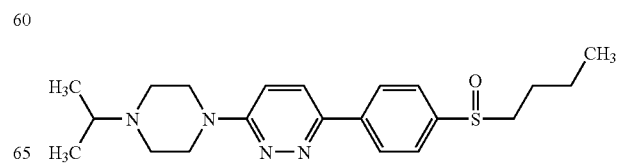

This compound was prepared according to General Procedure (A), starting from 1-isopropylpiperazine and 3-[4-(butane-1-sulfinyl)phenyl]-6-chloropyridazine, prepared according to General Procedure (C). The compound was isolated as its hydrochloride salt.

$^1$H NMR (d$_6$-DMSO): δ 0.87 (t, 3H), 1.26-1.50 (m, 9H), 1.65 (m, 1H), 2.83 (m, 1H), 3.02 (m, 1H), 3.18 (m, 2H), 3.45-3.60 (m, 3H), 3.68 (broad t, 2H), 4.64 (broad d, 2H), 7.74-7.86 (m, 3H), 8.26 (d, 2H), 8.32 (d, 1H), 11.41 (broad s, 1H); HPLC: R$_t$=5.52 min.

Example 7

3-(4-Isopropylpiperazin-1-yl)-6-[4-(propane-1-sulfonyl)phenyl]pyridazine

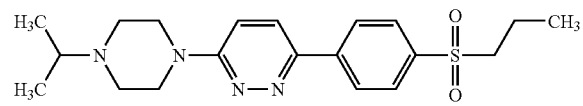

This compound was prepared according to General Procedure (A), starting from 1-isopropylpiperazine and 3-chloro-6-[4-(propane-1-sulfonyl)phenyl]pyridazine, prepared according to General Procedure (C). The compound was isolated as its hydrochloride salt.

$^1$H NMR (d$_6$-DMSO): δ 0.94 (t, 3H), 1.33 (d, 6H), 1.59 (m, 2H), 3.17 (m, 2H), 3.45-3.60 (m, 3H), 3.68 (broad t, 2H), 4.67 (broad d, 2H), 7.74 (d, 1H), 8.02 (d, 2H), 8.81 (d, 1H), 8.84 (d, 2H), 11.44 (broad s, 1H); HPLC: R$_t$=5.60 min.

Example 8

3-(4-Isopropylpiperazin-1-yl)-6-[4-(propane-1-sulfinyl)phenyl]pyridazine

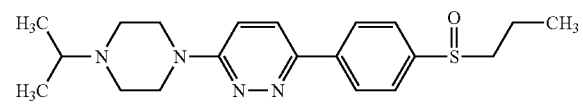

This compound was prepared according to General Procedure (A), starting from 1-isopropylpiperazine and 3-chloro-6-[4-(propane-1-sulfinyl)phenyl]pyridazine, prepared according to General Procedure (C). The compound was isolated as its hydrochloride salt.

$^1$H NMR (d$_6$-DMSO): δ 0.98 (t, 3H), 1.33 (d, 6H), 1.50 (m, 1H), 1.70 (m, 1H), 2.82 (m, 1H), 2.99 (m, 1H), 3.18 (m, 2H), 3.45-3.60 (m, 3H), 3.69 (broad t, 2H), 4.65 (broad d, 2H), 7.75-7.85 (m, 3H), 8.26 (d, 2H), 8.32 (d, 1H), 11.47 (broad s, 1H); HPLC: R$_t$=4.76 min.

Pharmacological Methods

The ability of the compounds to interact with the histamine H3 receptor can be determined by the following in vitro binding assays.

Binding Assay I

Rat cerebral cortex is homogenized in ice cold K-Hepes, 5 mM MgCl$_2$ pH 7.1 buffer. After two differential centrifugations the last pellet is resuspended in fresh Hepes buffer containing 1 mg/ml bacitracin. Aliquots of the membrane suspension (400 µg/ml) are incubated for 60 min at 25° C. with 30 pM [$^{125}$I]-iodoproxifan (a known histamine H3 receptor antagonist) and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analyzed by non-linear regression analysis.

Binding Assay II

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter. Male Wistar rats (150-200 g) are decapitated, and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM MgCl$_2$ pH 7.1 (KOH)+1 mg/ml bacitracin) using an Ultra-Turrax homogenizer for 30 seconds. The homogenate is centrifuged at 140 g in 10 min. The supernatant is transferred to a new test tube and centrifuged for 30 min at 23 000 g. Pellet is resuspended in 5-10 ml Hepes buffer, homogenized and centrifuged for 10 min at 23 000 g. This short centrifugation step is repeated twice. After the last centrifugation the pellet is resuspended in 2-4 ml Hepes buffer and the protein concentration is determined. The membranes are diluted to a protein concentration of 5 mg/ml using Hepes buffer, aliquoted and stored at −80° C. until use. 50 µl test-compound, 100 µl membrane (200 µg/ml), 300 µl Hepes buffer and 50 µl R-α-methyl[$^3$H]histamine (1 nM) are mixed in a test tube. The compounds to be tested are dissolved in DMSO and further diluted in H$_2$O to the desired concentrations. Radioligand and membranes are diluted in Hepes buffer+1 mg/ml bacitracin. The mixture is incubated for 60 min at 25° C. Incubation is terminated by addition of 5 ml ice-cold 0.9% NaCl, followed by rapid filtration through Whatman GF/B filters pre-treated for 1 hour with 0.5% polyethyleneimine. The filters are washed with 2×5 ml ice-cold NaCl. To each filter is added a 3 ml scintillation cocktail, and the retained radioactivity is measured with a Packard Tri-Carb beta counter.

IC$_{50}$ values are calculated by non-linear regression analysis of binding curves (6 points minimum) using the windows program GraphPad Prism, GraphPad software, USA.

Binding Assay III

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% CO$_2$. Before harvesting, the confluent cells are rinsed with PBS and incubated with Versene (proteinase, GIBCO-BRL) for approximately 5 min. The cells are flushed with PBS and DMEM and the cell suspension collected in a tube and centrifuged for 5-10 min at 1500 rpm in a Heraeus Sepatech Megafuge 1.0. The pellet is resuspended in 10-20 vol. Hepes buffer [20 mM Hepes, 5 mM MgCl$_2$, pH 7.1 (KOH)] and homogenized for 10-20 seconds using an Ultra-Turrax homogenizer. The homogenate is centrifuged for 30 min at 23 000 g. The pellet is resuspended in 5-10 ml Hepes buffer, homogenized 5-10 seconds with the Ultra-Turrax and centrifuged for 10 min at 23 000 g. Following this centrifugation step, the membrane pellet is resuspended in 2-4 ml Hepes buffer, homogenized with a syringe or Teflon homogenizer, and the protein concentration determined. The membranes are diluted to a protein concentration of 1-5 mg/ml in Hepes buffer, aliquoted and kept at −80° C. until use.

Aliquots of the membrane suspension are incubated for 60 min at 25° C. with 30 pM [$^{125}$I]-iodoproxifan (a known compound with high affinity for the H3 receptor) and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by non-linear regression analysis. When tested, the present compounds of the formula (I) generally show a high binding affinity to the histamine H3 receptor.

Preferably, the compounds according to the invention have an $IC_{50}$ value as determined by one or more of the assays of less than 10 µM, more preferably less than 1 µM, and still more preferably less than 500 nM, such as less than 100 nM.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G 418 at 37° C. and 5% $CO_2$.

The H3 receptor expressing cells are washed once with phosphate buffered saline (PBS) and harvested using versene (GIBCO-BRL). PBS is added and the cells are centrifuged for 5 min at 188 g. The cell pellet is resuspended in stimulation buffer to a concentration of $1\times10^6$ cells/ml. cAMP accumulation is measured using the Flash Plate® cAMP assay (NEN™ Life Science Products). The assay is generally performed as described by the manufacturer. Briefly, 50 µl cell suspension is added to each well of the Flashplate which also contained 25 µl 40 µM isoprenaline, to stimulate cAMP generation, and 25 µl of test compound (either agonists or inverse agonists alone, or agonist and antagonist in combination). The assay can be run in "agonist-mode" in which the test compound is added, in increasing concentration, on its own, to the cells, and cAMP is measured. If cAMP goes up, the compound in question is an inverse agonist; if CAMP does not change, it is a neutral antagonist, and if CAMP goes down, it is an agonist. The assay can also be run in the "antagonist-mode" in which a test compound is added, in increasing concentrations, together with increasing concentrations of a known H3 agonist (e.g. RAMHA). If the test compound is an antagonist, increasing concentrations of it cause a right-ward shift in the H3-agonist's dose-response curves. The final volume in each well is 100 µl. Test compounds are dissolved in DMSO and diluted in $H_2O$. The mixture is shaken for 5 min, and allowed to stand for 25 min at room temperature. The reaction is stopped with 100 µl "Detection Mix" per well. The plates are then sealed with plastic, shaken for 30 min, allowed to stand overnight, and finally the radioactivity is counted in the Cobra II auto gamma topcounter. $EC_{50}$ values are calculated by non-linear regression analysis of dose response curves (6 points minimum) using GraphPad Prism. Kb values are calculated by Schild plot analysis.

Functional Assay II

The ability of the compounds to bind and interact with the human H3 receptor as agonists, inverse agonists and/or antagonists, is determined by a functional assay, named [$^{35}$S] GTPγS assay. The assay measures the activation of G proteins by catalyzing the exchange of guanosine 5'-diphosphate (GDP) by guanosine 5'-triphosphate (GTP) at the α-subunit. The GTP-bounded G proteins dissociate into two subunits, $G\alpha_{GTP}$ and Gβγ, which in turn regulate intracellular enzymes and ion channels. GTP is rapidly hydrolysed by the Gα-sub-unit (GTPases) and the G protein is deactivated and ready for a new GTP exchange cycle. To study the function of ligand-induced G protein coupled receptor (GPCR) activation by an increase in guanine nucleotide exchange at the G proteins, the binding of [$^{35}$S]-guanosine-5'-O-(3-thio) triphosphate [$^{35}$S] GTPγS, a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor. The cells are washed twice in PBS, harvested with PBS+1 mM EDTA, pH 7.4 and centrifuged at 1000 rpm for 5 min. The cell pellet is homogenized in 10 ml ice-cold Hepes buffer (20 mM Hepes, 10 mM EDTA pH 7.4 (NaOH)) using an Ultra-Turrax homogenizer for 30 seconds and centrifuged for 15 min at 20.000 rpm. Following this centrifugation step, the membrane pellet is resuspended in 10 ml ice-cold Hepes buffer (20 mM Hepes, 0.1 mM EDTA pH 7.4 (NaOH)) and homogenized as described above. This procedure is repeated twice except for the last homogenization step, the protein concentration is determined, and membranes are diluted to a protein concentration of 2 mg/ml, aliquoted and kept at −80° C. until use.

In order to study the presence and the potency of an inverse agonist/antagonist, the H3-receptor agonist ligand R-α-methyl histamine (RAMHA) is added. The ability of the test compound to counteract the effect of RAMHA is measured. When studying the effect of an agonist, RAMHA is not added to the assay medium. The test compound is diluted in the assay buffer (20 mM HEPES, 120 mM NaCl, 10 mM $MgCl_2$ pH 7.4 (NaOH)) at various concentrations followed by addition of $10^{-8}$ nM RAMHA (only in the case where an inverse agonist/antagonist is examined), 3 µM GDP, 2.5 µg membranes, 0.5 mg SPA beads and 0.1 nM [$^{35}$S] GTPγS, and incubation for 2 hours with gentle shaking at room temperature. The plates are centrifuged at 1500 rpm for 10 min and the radioactivity is measured using a Topcounter. The results are analyzed by non-linear regression and the $IC_{50}$ value is determined. RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by $10^{-8}$ M RAMHA is measured as a decrease in radioactivity signal. The $IC_{50}$ value determined for an antagonist is the ability of this compound to inhibit the effect of $10^{-8}$M RAMHA by 50%. In the agonist test, the ability of increasing amounts of test compound is measured as an increase in radioactivity signal. The $EC_{50}$ value determined for an agonist is the ability of this compound to increase the signal by 50% of the maximal signal that is obtained by $10^{-5}$ M RAMHA.

Preferably, the antagonists and agonists according to the invention have an $IC_{50}/EC_{50}$ value (as determined by one or more of the assays described above) of less than 10 μM, more preferably less than 1 μM, and still more preferably less than 500 nM, such as less than 100 nM.

The Open Cage Schedule-Fed Rat Model

The ability of the present compounds to reduce weight is determined using the in vivo open cage Schedule-fed rat model.

Sprague-Dawley (SD) male rats of an age of about 1½ to 2 months and a weight of about 200-250 g are purchased from Møllegård Breeding and Research Centre A/S (Denmark). On arrival they are allowed some days of acclimatisation before being placed in individual open plastic cages. They are habituated to the presence of food (Altromin pelleted rat chow) in their home cage for only 7 hours each day (from 07.30 to 14.30, seven days a week). Water is present ad libitum. Once the consumption of food has stabilised after 7 to 9 days, the animals are ready for use.

Each animal is used only once to avoid carry-over effects between treatments. During the test sessions, the test compound is administered intraperitoneally or orally 30 min before the start of the sessions. One group of animals is administered the test compound at different doses, and a control group of animals receives vehicle. Food and water intake are monitored at 1, 2 and 3 hours post administration.

Any side effects (manifested as barrel-rolling, bushy fur etc.) may rapidly be detected, since the animals are kept in transparent plastic cages to enable continuous monitoring.

What is claimed is:

1. A compound according to formula I

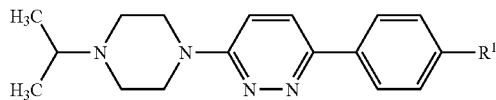

[I]

wherein $R^1$ is independently selected from fluoro, bromo, jodo, hydroxy, trifluoromethoxy, $C_{2-6}$-alkoxy, $C_{1-6}$-alkyl, amino, $C_{2-6}$-alkylsulfanyl, $C_{2-6}$-alkylsulfinyl, $C_{2-6}$-alkylsulfonyl, $C_{1-6}$-alkylamino, di-$C_{1-6}$-alkylamino, cyano, nitro, aryl, heteroaryl and $C_{3-8}$-cycloalkyl;

and pharmaceutically acceptable salts, solvates and prodrugs thereof.

2. A compound according to claim 1, wherein $R^1$ represents bromo or cyano.

3. A pharmaceutical composition comprising, as an active ingredient, at least one compound according to claim 1, together with one or more pharmaceutically acceptable carriers or excipients.

4. A pharmaceutical composition according to claim 3, in unit dosage form, comprising from about 0.05 mg to about 1000 mg, from about 0.1 mg to about 500 mg, or from about 0.5 mg to about 200 mg of a compound according to claim 1.

5. A method for the treatment of disorders or diseases related to the H3 histamine receptor selected from the following: obesity, suppression of appetite or satiety induction, osteoarthritis, bulimia, binge eating, anorexia, impaired glucose tolerance (IGT), type 2 diabetes, allergic rhinitis, narcolepsy, asthma, and diarrhea, the method comprising administering to a subject in need thereof an effective amount of a compound according to claim 1.

6. A method according to claim 5, wherein the effective amount of the compound is in the range of from about 0.05 mg to about 2000 mg, from about 0.1 mg to about 1000 mg, or from about 0.5 mg to about 500 mg per day.

7. A method according to claim 5, for the treatment of obesity.

8. A method according to claim 5, for the suppression of appetite or for satiety induction.

9. A method according to claim 5, for the treatment of Impaired Glucose Tolerance (IGT).

10. A method according to claim 5, for the treatment of type 2 diabetes.

11. A method according to claim 5, for the treatment of allergic rhinitis or anorexia.

12. A method according to claim 5, for the treatment of narcolepsy.

* * * * *